US011185712B2

(12) United States Patent
Muti

(10) Patent No.: US 11,185,712 B2
(45) Date of Patent: Nov. 30, 2021

(54) PULSED ELECTROMAGNETIC EMISSION DEVICE

(71) Applicant: KARNAK MEDICAL S.R.L., Milan (IT)

(72) Inventor: Elio Muti, Milan (IT)

(73) Assignee: KARNAK MEDICAL S.R.L., Milan (IT)

( * ) Notice: Subject to any disclaimer, the term of this patent is extended or adjusted under 35 U.S.C. 154(b) by 253 days.

(21) Appl. No.: 16/464,076

(22) PCT Filed: Oct. 12, 2017

(86) PCT No.: PCT/IB2017/056322
§ 371 (c)(1),
(2) Date: May 24, 2019

(87) PCT Pub. No.: WO2018/096412
PCT Pub. Date: May 31, 2018

(65) Prior Publication Data
US 2019/0381332 A1   Dec. 19, 2019

(30) Foreign Application Priority Data

Nov. 25, 2016   (IT) .......................... 102016000119648

(51) Int. Cl.
*A61N 2/02* (2006.01)
*A61N 2/00* (2006.01)
*A61N 5/06* (2006.01)

(52) U.S. Cl.
CPC ............... *A61N 2/02* (2013.01); *A61N 2/002* (2013.01); *A61N 2005/0647* (2013.01); *A61N 2005/0663* (2013.01)

(58) Field of Classification Search
CPC .... A61N 2005/0647; A61N 2005/0663; A61N 2/002; A61N 2/02
See application file for complete search history.

(56) References Cited

U.S. PATENT DOCUMENTS

| 6,443,978 B1* | 9/2002 | Zharov | A61N 5/0616 607/91 |
| 2005/0182287 A1* | 8/2005 | Becker | A61N 2/02 600/13 |

FOREIGN PATENT DOCUMENTS

| ES | 1 141 685 U | 7/2015 |
| WO | 2008/049775 A1 | 5/2008 |
| WO | 2016/163776 A1 | 10/2016 |

* cited by examiner

*Primary Examiner* — Christine H Matthews
*Assistant Examiner* — Joshua Daryl D Lannu
(74) *Attorney, Agent, or Firm* — Vorys, Sater, Seymour & Pease

(57) ABSTRACT

A pulsed electromagnetic emission device is provided, which is configured to be placed in adherence with at least a part of the body of a user, including at least a first emitter configured to emit at least one pulsed magnetic field and at least a second emitter configured to generate at least one luminous signal, wherein the second emitter is at least partly immersed in the pulsed magnetic field when the first emitter emits the pulsed magnetic field.

10 Claims, 2 Drawing Sheets

PULSED ELECTROMAGNETIC EMISSION DEVICE

The present invention relates to a pulsed electromagnetic emission device of the type specified in the preamble of the first claim.

In particular, the invention relates to a device adapted to induce electromagnetic impulses on a user, which interact with the body cells for beneficial purposes.

It is known that the human body is generally subject to inflammatory conditions and ageing, which undermine its wellbeing with repercussions on each person's everyday life.

In particular, these unpleasant natural conditions are due, in the absence of specific diseases, to variations in the body cell potentials which can result in an increased sensitivity to anxiety states, insecurity and sadness, as well as in a reduction of the immune defences and the ability to concentrate.

In detail, the cell inflammatory condition is caused by an undesired accumulation of positive charges. The excess of these positive electrical charges creates, as said, the inflammatory condition and, over time, cellular stress with an increase in the value of the cell membrane potential.

The optimal cell membrane potential is substantially equal to −90 mV. When the latter reaches the value of −20 mV, cell degeneration begins, which continues up to the zero value at which cell death occurs.

It is therefore essential that the optimum thrust at the physical level be provided with an electromagnetic field directed to maintain the optimal characteristics of the body cells.

However, in the current state of the art, therapeutic techniques involving the use of electromagnetic fields are well known.

These techniques are known by the term "magnetotherapy" and relate, in particular, to the application of pulsed magnetic fields on the human body in order to regenerate the potential of the body cells.

The devices so far provided for the implementation of said therapeutic procedures therefore generally involve the use of solenoids inside which a pulsed current flow for generating magnetic fields with greater intensity along the axis of the solenoid itself.

In particular, generally, the magnetic fields adopted for such techniques have high intensities even up to values around 10 T.

Typically, these solenoids are thus applied on the body inside circular diffusers or handle tools or headphones, which allow them to be placed on the head of a user. An example of what is described is included within patent application PC1991A000007.

In detail, the application describes an auricular stimulator, which generates electromagnetic waves healthy for the body by reactivating and balancing the electromagnetic frequencies emitted by the brain to stimulate vital processes. Furthermore, the emission frequencies of the device remain at values lower than 18 Hz, i.e. within the range of extremely low (ELF) and ultra low (ULF) frequencies, in full harmony with the frequencies expressed by the organic functions.

The described prior art has a few major drawbacks.

In particular, magnetotherapy devices can only emit magnetic pulses on a user's body and are suitable to perform this function only.

Therefore, a further major drawback is that the devices of the current state of the art are not able to stimulate the cells of the human body by means of different types of stimuli.

Similar devices are described in U.S. Pat. No. 6,443,978 and in PCT application WO-A-2008/049775.

In this context, the technical task underlying the present invention is to devise a pulsed electromagnetic emission device, which is capable of substantially obviating the above-mentioned drawbacks.

Within the scope of said technical task, a major object of the invention is to obtain a device, which allows to regenerate the potential of the body cells of a user in an enhanced manner compared to the current state of the art.

Another major object of the invention is to provide a pulsed electromagnetic emission device, which allows the body of a user to be stimulated with stimuli that are not exclusively magnetic.

In conclusion, a further object of the invention is to provide a device, which is suitable to interact with the body of a user by means of stimuli acting synergistically with each other.

The technical task and the specified objects are achieved by means of a pulsed electromagnetic emission device as claimed in the appended claim 1. Preferred embodiments are described in the dependent claims.

The features and advantages of the invention will be apparent from the detailed description of preferred embodiments of the invention, with reference to the accompanying drawings, in which.

Figure 1:
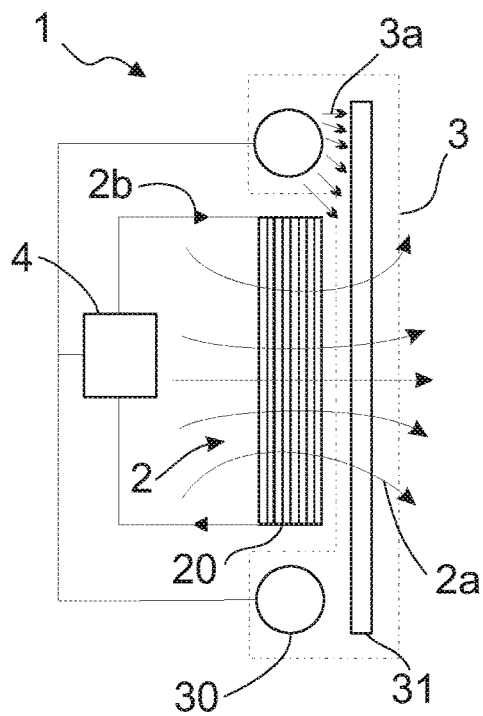
FIG. 1 shows the pulsed electromagnetic emission device.
Figure 2:
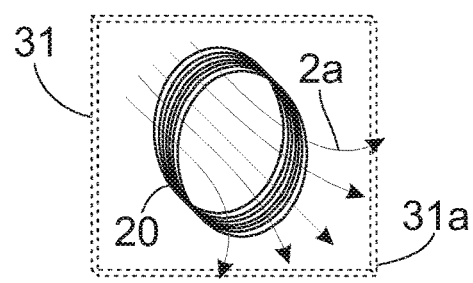
FIG. 2 illustrates the solenoid and the plate in perspective.
Figure 3:
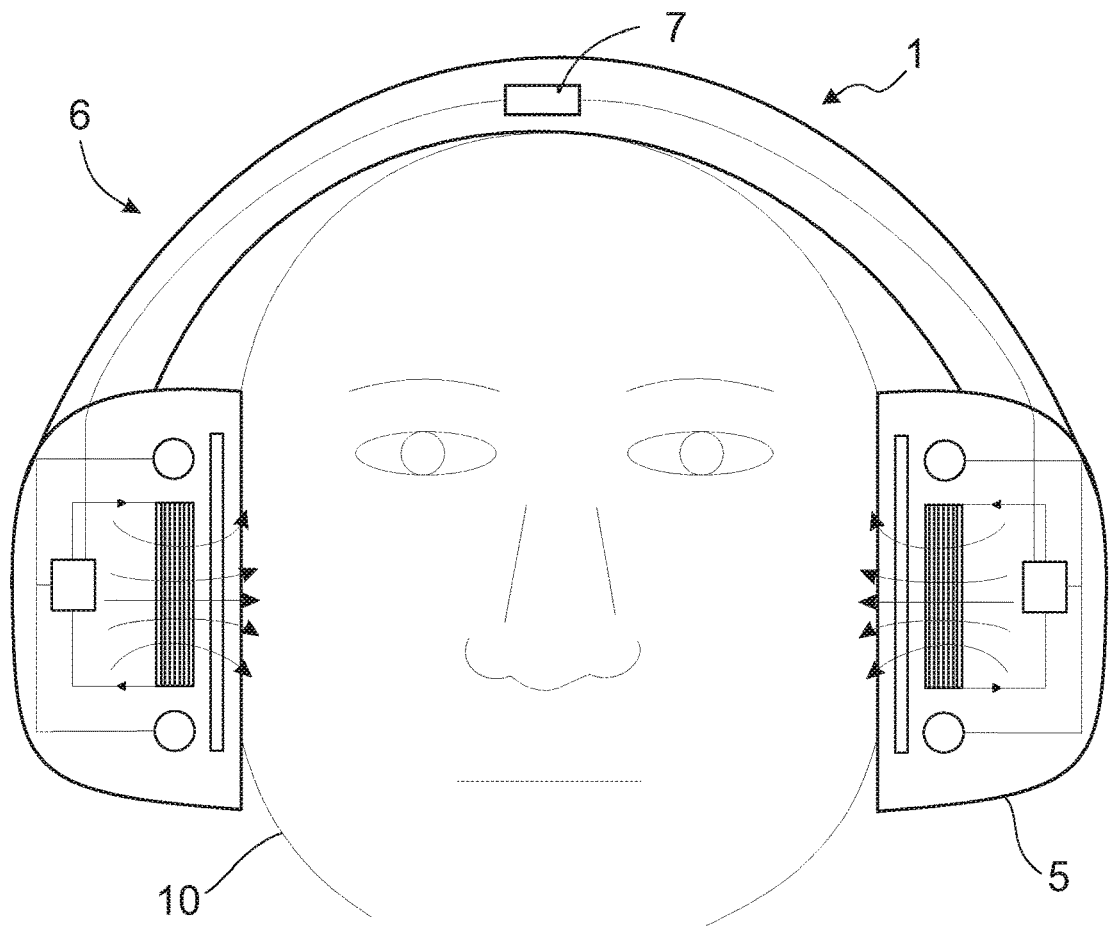
FIG. 3 is the device according to the invention in an auricular headphone configuration.
Figure 4:
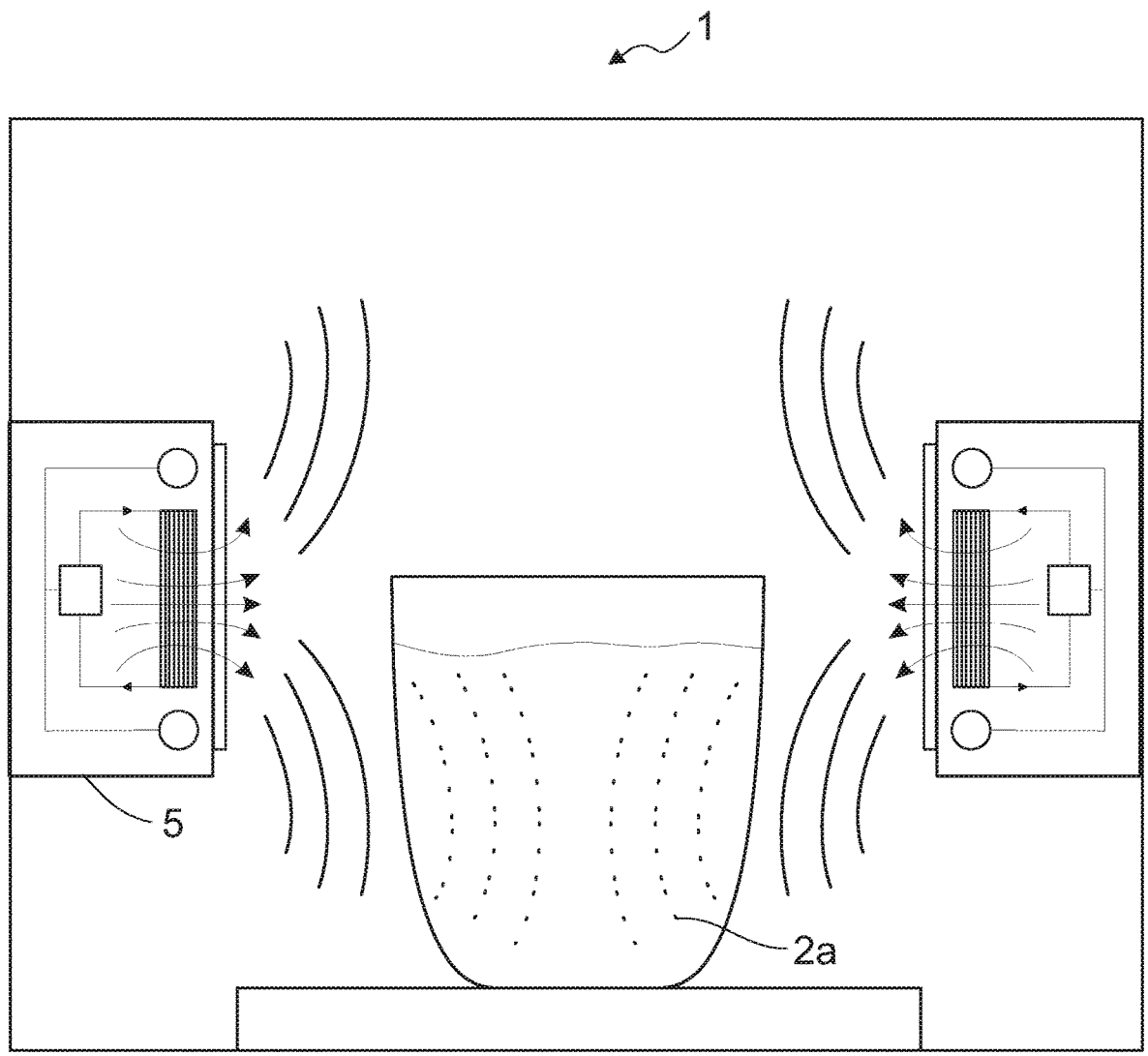
FIG. 4 is the device according to the invention configured as a magnetization box.

In the present document, the measures, values, shapes and geometric references (such as perpendicularity and parallelism), when associated with terms like "about" or other similar terms such as "almost" or "substantially", are to be understood as unless measurement errors or inaccuracies due to production and/or manufacturing defects and, especially, unless a slight difference from the value, the measure, the shape, or the geometric reference with which it is associated. For example, these terms, if associated with a value, preferably indicate a difference not exceeding 10% of the value itself.

Furthermore, when used, terms such as "first", "second", "higher", "lower", "main" and "secondary" do not necessarily identify an order, a priority relationship or a relative position, but can simply be used to distinguish more clearly the different components from each other.

With reference to the Figures, the pulsed electromagnetic emission device according to the invention is indicated as a whole by the numeral 1.

The pulsed electromagnetic emission device 1 is preferably suitable to be placed in adherence with an object 10 such as at least a part of the body of a user or even of food, water, drinkable liquids or animals.

For example, the device 1 can be positioned in the area of the head of a user 10 or in other parts of the body, such as limbs or joints that are for example affected by diffuse inflammatory conditions.

However, the device 1 is not only intended for therapeutic use, but may also be intended for the treatment of foods, beverages, liquids, dietary supplements and materials for prostheses.

For example, the device 1 can be placed in adherence with an apple, or it can be put close to a liquid, such as water, to enrich the latter and enhance the anti-oxidants effects.

In general, the device 1 can be applied to materials, liquid compositions, creams and gels, as well as prostheses, in order to create the conditions for frequency harmony (consistency domains) by increasing the compliance and biocompatibility of the treated materials with the human body.

The device 1 also comprises at least a first emitter 2 and a second emitter 3.

The first emitter 2, in particular, is preferably suitable to emit at least one pulsed magnetic field 2a. This pulsed magnetic field can be generated by different types of elements, which define their field lines.

Preferably, the first emitter 2 comprises at least one conductive filament. Thus, the conductive filament is for example suitable to allow the passage, inside it, of a pulsed current 2b.

This pulsed current 2b is thus suitable to generate the pulsed magnetic field 2a. The pulsed current 2b may have different types of shapes. For example, it can be a current consisting of a square, triangle, sawtooth, or canonical waveform. Preferably, the pulsed current 2b is a medium-frequency triangle wave. Medium-frequency triangle wave is intended to mean that the pulsed current 2b comprises triangular peaks, which are only positive or only negative, spaced by zero-value sections.

Moreover, the pulsed current 2b has a maximum intensity preferably comprised between 1 dA and 1 daA, more suitably 1 A, and a frequency less than 25 Hz and more suitably less than 19 Hz.

Therefore, the pulsed magnetic field 2a preferably has the same pattern as the pulsed current 2b and the same frequency, the intensity being dependent on the type of conductor chosen for the first emitter 2.

Also preferably, the pulsed magnetic field 2a has an intensity less than 10 G or $10^{-3}$ T.

Preferably, the first emitter 2 is a solenoid 20 and therefore the conductive filament is wound with continuity into coils forming said solenoid 20.

The pulsed magnetic field 2a preferably generated by the solenoid 20 is therefore dependent on the dimensions of the solenoid 20 itself and on the number of coils formed by the conductive filament.

Moreover, the pulsed magnetic field 2a is preferably maximum within the solenoid 20 itself.

The second emitter 3 is preferably suitable to generate at least one luminous signal 3a.

This luminous signal 3a is for example a pulsed signal or a continuous signal variable in frequency and therefore can exhibit tones of different brightness or colour.

The second emitter 3 comprises, for example, at least one source 30 suitable to emit the luminous signal 3a.

The source 30 can be of different types. For example, it may be an incandescent bulb or a fluorescent lamp and still more, but more preferably the source 30 is a LED source.

Most suitably, the source 30 is a LED source suitable to generate multicoloured frequencies in a controlled manner and is for example of the RGB type.

The source 30 can also be suitable to emit light outside the visible range, such as infrared and/or ultraviolet rays or more.

The second emitter 3 further preferably also comprises at least one plate 31.

The term plate is intended to mean a geometrical object in which two dimensions prevail significantly with respect to the third dimension.

Therefore, this plate 31 defines, for example, a diffusion surface 31a which is suitable to diffuse said luminous signal 3a.

This diffusion surface 31a is essentially, for example, the area defined by the prevailing dimensions of the plate 31.

Furthermore, the plate 31 can be made of different materials that allow the diffusion of light such as, for example, glass. Preferably, the plate 31 is made of a polymeric material, and more suitably of PVC.

Moreover, the plate 31 is for example white, although it can be chosen in different colours or even transparent. The plate 31 could also be completely opaque and diffuse the light only towards the inside of the device.

The plate 31 can be arranged inside the device according to different configurations. Preferably, the plate 31 is interposed between the first emitter 2 and at least part of the body of the user 10, if in use for therapeutic purposes, or between the first emitter 2 and the outer surface of the food or the liquid container on which the device 1 carries out the treatment.

In particular, in addition, the plate 31 is positioned for example close to the first emitter 2 so that the pulsed magnetic field 2a generated by the first emitter 2 crosses the diffusion surface 31a. Therefore, the pulsed magnetic field 2a and the diffusion surface 31a define a pulsed magnetic field flow, which is substantially other than zero when the pulsed magnetic field 2a has a value other than zero.

For example, assuming that the first emitter 2 is a solenoid 20, the plate 31 can be laid on one of the two hollow bases of the solenoid so that the higher-intensity lines of the pulsed magnetic field 2a cross the diffusion surface 31a perpendicularly.

In general, the second emitter 3 is arranged close to the first emitter 2.

In particular, the second emitter 3 is preferably at least partly immersed in the pulsed magnetic field 2a when the first emitter 2 emits the pulsed magnetic field 2a, i.e. is in operation.

As said, preferably, the part immersed in the pulsed magnetic field 2a consists of the portion of the plate 31 arranged at the solenoid output.

As regards the source or sources 30, it/they can be arranged inside the first emitter, i.e. for example inside the solenoid, or be arranged externally thereto.

Preferably, at least one source 30 is arranged outside the first emitter 2, and preferably the sources 30 are two and are arranged below and above the solenoid 20.

The device 1 further comprises at least one current generator 4.

The current generator 4 is for example suitable to generate the pulsed current 2b and is therefore preferably placed in electrical connection with the first emitter 2. The current generator 4 may further supply at least one source 30. For example, the generator 4 may thus be in electrical connection with at least one source 30 alone or with both the source 30 and the first emitter 2.

The device 1 may also comprise control means 7.

The control means 7 can be, for example, microchips or microprocessors designed to control the emission of current at the first emitter 2 and the second emitter 3.

This, for example, allows the interaction between the pulsed magnetic field 2a and the luminous signal 3a to be defined and modified.

For example, the control means 7 may also be suitable to control the source 30, and in particular, for example, suitable to control the multicoloured frequencies of the LEDs when of the RGB type.

The device 1 may also comprise a plurality of first emitters 2 and second emitters 3. In particular, the device 1 comprises, for example, two first emitters 2 and two second emitters 3. The device 1 thus comprises, for example in this configuration, two diffusers 5.

The diffusers 5 each preferably comprise at least a first emitter 2 and a second emitter 3.

The diffusers 5 can thus be shaped cups for the application of the device 1 on the body or on foods and beverages. In addition, they can be auricular type diffusers and hence the device 1 can substantially consist of auricular headphones 6.

The auricular headphones 6 can therefore be applied on at least a part of the body of a user 10. Preferably, the auricular headphones 6 can be applied to the head of a user and therefore the emissions coming from the diffusers 5 are directed towards the head.

Preferably, the diffusers 5 face each other and therefore preferably generate two pulsed magnetic fields in opposition to one another.

The diffusers 5 can thus be controlled by the control means 7 so that the emissions coming from the former can be operated and/or differentially varied.

The operation of the device 1, previously described in structural terms, is as follows. The device 1 can be applied to food or drinks or even on a user 10.

Once operated, it enables the emission of pulsed magnetic fields that cross a diffusion surface 31a on which a luminous signal 31a is diffused.

The luminous signal 3a and the pulsed magnetic field 2a arrive together synergistically at the surface of the body of a user 10 or at the outer surface of food or beverage containers.

This allows the potential of the body cells to be regenerated, for example, by treatment of the same with differential pulsed magnetic fields 2a coming from the diffusers 5, with an overall slightly negative polarity.

This makes it possible to lower the membrane potential of the cells, thus enhancing their functionality.

The invention provides a new use consisting in the treatment of foods and drinks. In particular, these foodstuffs acquire, through the diffusion of the pulsed magnetic fields 2a and the luminous signals 3a, enhanced antioxidant effects, and are found to be more digestible within the body and to provide an additional frequency intake functional therefor.

It can also be applied on materials for prostheses in order to place the atoms of matter in frequency harmony and favour a greater compliance of the body on which they are applied.

The pulsed electromagnetic emission device 1 according to the invention achieves important advantages.

In fact, the device 1 allows the cells of the body subjected to ageing or wear to be regenerated by lowering the potential of the body and neuronal cells.

Moreover, the device 1 enables both therapeutic treatments as well as treatments of foods, beverages, liquids, supplements and solutions such as creams, gels and materials for prostheses, by means of pulsed magnetic fields 2a and luminous signals 3a that are synergistically directed to the body of a user 10 or to foods and beverages.

The application of luminous signals 3a driven by the pulsed magnetic fields 2a allows the regenerative capacity to be increased compared to devices that exclusively use magnetic fields.

In conclusion, the device 1 advantageously exploits ELF and ULF frequency magnetic fields in full compliance with the cellular and neuronal functions, without the same frequency information being detrimental to the body.

In fact, the device 1 favours full compliance, for example, of the body through the emission of mild intensity magnetic fields (less than 10 G), compared to those adopted in the scope of the prior art (up to 10 T), which penetrate the cell resonance windows, or Adey's windows, in addition to overcoming the resistance offered by the living being and the matter itself to electromagnetic frequency stimulation by the use of the emitted coloured scales.

The invention is susceptible of variations falling within the scope of the inventive concept as defined by the claims.

For example, the device 1 may not consist of auricular headphones 6, but may comprise a single diffuser 5 and be, for example, an elastic band that can be positioned as desired on the body of a user 10.

Alternatively, the device 1 can comprise one or more diffusers 5 integrated in a magnetization box for foods, liquids, supplements, beverages, creams, gels and materials for prostheses.

For example, the device 1 in the latter configuration could be suitable for the treatment of titanium prostheses, widely used in the biomedical field, or silicone gels, compound dental materials or the like, in order to increase their biocompatibility with the human body, thus reducing the possibility of rejection by the body.

In this context, all the details are replaceable by equivalent elements and the materials, shapes and dimensions may be any materials, shapes and dimensions.

The invention claimed is:

1. A pulsed electromagnetic emission device configured to be placed in adherence with an object, comprising at least:
    two diffusers facing each other and adapted to generate pulsed magnetic fields in opposition to each other,
    wherein said object can be positioned between said two diffusers,
    wherein each of said diffusers comprises:
        a first emitter configured to emit said pulsed magnetic field fields, and
    at least one current generator,
    and wherein each of said diffusers comprises:
        a second emitter configured to generate at least one luminous signal, and comprising at least one source configured to emit said at least one luminous signal and at least one plate defining a diffusion surface, said diffusion surface being configured to diffuse said at least one luminous signal, and
    said at least one plate is interposed between said first emitter and said object, said object to be treated with said pulsed magnetic fields.

2. The device according to claim 1, wherein said first emitter comprises at least one conductive filament, said at least one conductive filament being configured to allow a passage, inside said at least one conductive filament, of a pulsed current to generate said pulsed magnetic fields.

3. The device according to claim 2, wherein said first emitter is a solenoid.

4. The device according to claim 3, wherein said pulsed magnetic fields cross said diffusion surface, said pulsed magnetic fields and said diffusion surface defining a non-zero pulsed magnetic field flow when said pulsed magnetic fields have a value other than zero.

5. The device according to claim 4, wherein said at least one current generator is configured to generate a pulsed current and is placed in electrical connection with said first emitter.

6. The device according to claim 5, wherein said diffusers are auricular diffusers and said diffusers consists of auricular headphones.

7. The device according to claim 1, wherein said first emitter is a solenoid.

8. The device according to claim 1, wherein said pulsed magnetic fields cross said diffusion surface, said pulsed magnetic fields and said diffusion surface defining a non-zero pulsed magnetic field flow when said pulsed magnetic fields have a value other than zero.

9. The device according to claim 1, wherein said at least one current generator is configured to generate a pulsed current and is placed in electrical connection with said first emitter.

10. The device according to claim 1, wherein said diffusers are auricular diffusers and said diffusers consists of auricular headphones.

* * * * *

UNITED STATES PATENT AND TRADEMARK OFFICE
CERTIFICATE OF CORRECTION

PATENT NO. : 11,185,712 B2
APPLICATION NO. : 16/464076
DATED : November 30, 2021
INVENTOR(S) : Muti Page 1 of 1

It is certified that error appears in the above-identified patent and that said Letters Patent is hereby corrected as shown below:

In the Claims

Claim 1, Column 6, Line 35, change as follows:
fields, and

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*